United States Patent [19]

Muench

[11] 4,071,521

[45] Jan. 31, 1978

[54] PROCESS FOR MAKING 2,6-DIFLUORO PYRIDINE

[75] Inventor: Terry G. Muench, Prescott, Ariz.

[73] Assignee: The Dow Chemical Company, Midland, Mich.

[21] Appl. No.: 716,864

[22] Filed: Aug. 23, 1976

[51] Int. Cl.² ............................................ C07D 213/04
[52] U.S. Cl. ...................... 260/290 HL; 260/294.8 G
[58] Field of Search ................................ 260/290 HL

[56] References Cited

U.S. PATENT DOCUMENTS 3,629,424   12/1971   Torba .................................... 424/263

FOREIGN PATENT DOCUMENTS 1,306,517   2/1973   United Kingdom ......... 260/290 HL

OTHER PUBLICATIONS

Fieser & Fieser, Reagents For Organic Synthesis, vol. I, Wiley Pub., pp. 375; 933 & 934.

*Primary Examiner*—Alan L. Rotman
*Attorney, Agent, or Firm*—Robert R. Stringham

[57] ABSTRACT

It has been found that practical rates of formation of 2,6-difluoropyridine from 2,6-dichloropyridine and KF can be attained without resort to catalysts, high temperatures or large excesses of KF, if:

a. dimethyl sulfoxide (DMSO) is employed as the reaction medium,
b. the reaction mixture contains less than 0.015 grams of HF and 0.5 grams of $K_2CO_3$ or $KHCO_3$ per 100 grams of KF and less than 0.5 grams of water per 100 grams of DMSO,
c. the difluoropyridine is distilled out as formed, and
d. the reaction mixture is intensely stirred and kept at a temperature of 175°–192° C.

10 Claims, No Drawings

PROCESS FOR MAKING 2,6-DIFLUORO PYRIDINE

BACKGROUND OF THE INVENTION

British patent specification No. 1,306,517 discloses a process for converting chloropyridines to fluoropyridines by reaction with alkali metal fluorides in polar, aprotic solvents at temperatures of from 160° to 250° C. The solvent may or may not be mixed with water and the reaction is carried out in the presence of an acid, base or organic hydroxy compound as an "initiator". The preferred solvent is sulfolane (tetramethylene sulfone) and the preferred initiator is ethylene glycol.

In the sole example in the patent of 2,6-difluoropyridine preparation, a 62% conversion of 2,6-dichloropyridine to the difluoro derivative is reported as having been obtained by refluxing a mixture of about 2 moles of the dichloropyridine and about 8 moles of anhydrous KF in sulfolane (containing 1.2 wt. percent of ethylene glycol) for 2 hours at 225-235° C.

Reaction temperatures as high as 225° are not particularly attractive for 2,6-difluoropyridine production. The boiling point of the latter compound is only about 125° at sea level and it is therefore necessary either to operate under a pressure at least equal to the (quite substantial) autogenous pressure of the reaction mixture or to allow the difluoro compound to distil out of the reaction mixture as formed and to provide for reflux return to avoid losses of the chloro/fluoro intermediate, which is also quite volatile. However, substantially lower reaction rates can be anticipated at lower temperatures. In fact, a reaction period of 25-30 hours is required to attain an 80% yield of the difluoropyridine at 150°, in DMSO, and much longer periods are required in other solvents, including sulfolane, at this temperature.

The use of DMSO as the reaction medium at higher temperatures is contraindicated by two considerations: (1) the solubility of KF in this solvent goes down, rather than up, as the temperature increases (see Table 1); and (2) DMSO is known (Traynelis et al., *J. Org. Chem.*, 29, 221 (1964)) to slowly decompose at reflux temperature (~189° C.) and (according to *Finger and Starr, J.A.C.S.*, 81, 2674 (1959)) to react with halogen compounds. Substantial alteration of DMSO would then be expected at elevated temperatures in the presence of such inherently reactive compounds as 2,6-difluoro- or 2-chloro-6-fluoropyridine.

On the other hand, if the reaction period could be sufficiently shortened by use of an appropriate catalyst, an unacceptable degree of solvent decomposition might not result. According to the British patent specification No. 1,306,517, ethylene glycol is the "initiator" of choice. Therefore, despite the fact that ethylene glycol is known (Traynelis et al., loc. cit.) to promote alteration of DMSO, an attempt was made to employ the glycol as a catalyst for the reaction of 2,6-dichloropyridine with KF in DMSO at 186° C. 74.35 and 13.3% yields, respectively, of the difluoro and chloro/fluoro products were attained in a reaction period of 5.5 hours. However, a total of about 11% of the dichloropyridine was found to have been converted to undesired, solvent-derived by-products. Accordingly, the use of such catalysts as ethylene glycol appears to be ruled out.

It is known that replacement of chloro substituents on aromatic rings by fluorine can be achieved at less elevated temperatures if the ring is also substituted with an activating group. Thus, Finger and Kruse reported (*J.A.C.S.*, 78, 6034 (1956)) that a 47% yield of a monofluoro derivative was obtained by reacting 2,4-dichloronitrobenzene with excess KF in DMSO (dimethyl sulfoxide) at 180° for 6 hours; they attributed this result to activation by the nitro group. Similarly, U.S. Pat. No. 3,629,424 discloses (Example 5) that 30 grams (a 34.7% yield) of 3,5-dichloro-2,6-difluoro-4-cyanopyridine was obtained by reacting 100 grams of tetrachloro-4-cyanopyridine in DMSO at 40–50° for 5 hours. However, no way of introducing a subsequently removable activating group in 2,6-dichloropyridine is evident.

An alternative possibility, which does not appear to have been considered, is that the materials ordinarily employed in the reaction may contain one or more impurities which act as "negative catalysts" and/or are conducive to DMSO alteration. For example, Traynelis et al (loc. cit.) reported that the decomposition of DMSO is accelerated by acids.

As ordinarily supplied, DMSO does not contain any detectable amounts of acids and 2,6-dichloropyridine is thermally stable and is commonly employed as a distilled, acid-free, starting material. Thus, if the exchange reaction is being effected by an acidic material, the latter must be introduced as an impurity, in the KF used. However, the highest acid (HF) content present, according to suppliers specifications, in any of the several grades of KF available is only 0.02%. Thus, acidic impurities in the KF would not appear to constitute an obvious source of difficulty.

Nevertheless, it has in fact been discovered that even reagent grade KF may contain sufficient amounts of HF to have a serious, adverse effect when the KF/alpha-chloropyridine reaction is carried out in DMSO at temperatures substantially above 150°.

OBJECTS OF THE INVENTION

A primary object of the present invention is to provide a method for preparing 2,6-difluoropyridine from 2,6-dichloropyridine (or 2-chloro-6-fluoropyridine) by which practical reaction rates can be attained without employing higher boiling solvents than DMSO, supra-atmospheric pressures, catalysts or large excesses of KF.

It is also an object to provide an improvement in the method of making 2,6-difluoropyridine by reacting KF and 2,6-dichloro- or 2-chloro-6-fluoropyridine in DMSO, whereby temperatures high enough to ensure practical reaction rates can be employed without experiencing substantial DMSO alteration and/or formation of substantial amounts of halopyridine-derived by-products.

A further object is to provide a process for making 2,6-difluoropyridine wherein the inclusion in the reaction mixture of materials which constitute a recovery or disposal problem, such as acids, bases and organic hydroxyl compounds, is avoided.

Yet another object is to provide a process of the preceding type which avoids or mitigates the corrosion problems inherent in the use of HF-containing or -generating materials at elevated temperatures.

SUMMARY OF THE INVENTION

The present invention is an improved process for making 2,6-difluoropyridine from 2,6-dichloro- or 2-chloro-6-fluoropyridine and alkali metal fluorides.

It has now been found that temperatures high enough to ensure practical rates of reaction between the preceding alpha-chloropyridines and KF in DMSO can be employed without experiencing substantial DMSO alteration and/or formation of substantial amounts of halopyridine-derived by-products, if the reaction mixture does not contain more than a negligible amount of HF-source materials or potassium carbonate.

More precisely, the invention may be defined as follows:

In the process of preparing 2,6-difluoropyridine by reacting KF with an alpha-chloropyridine which is 2,6-dichloro- or 2-chloro-6-fluoropyridine, in dimethyl sulfoxide (DMSO) at an elevated temperature, essentially in the absence of initiators or catalysts, and distilling out the difluoropyridine as formed, the improvement whereby distilled difluoropyridine yields of at least 90% can be attained in reaction periods of 15 hours or less, without employing large excesses of KF or temperatures so elevated as to result in substantial DMSO alteration, said improvement comprising carrying out the reaction by:

a. providing a mixture of solid KF particles and a solution, in DMSO, of said alpha-chloropyridine, said mixture containing
  1. less than such amount of any HF source materials as to provide a total of 0.015 grams of HF per 100 grams of KF;
  2. a total of less than 0.5 grams of $K_2CO_3$ and $KHCO_3$ per 100 grams of KF;
  3. less than 0.5 grams of water per 100 grams of DMSO; and
b. intensely stirring said mixture and maintaining the temperature thereof within the range of from about 175° to about 192°.

The meaning to be given the term "intensely stirring" in the foregoing definition (and in the claims appended to these specifications) is that the reaction mixture is stirred with sufficient vigor so that the distribution of the solid KF particles in the mixture is essentially uniform. That is, the amount of particulated KF present in any unit volume of the reaction mixture will be within the range of 95–105% of the amount present in any other unit volume. Methods of ensuring that an essentially uniform distribution is maintained are discussed subsequently herein.

Advantageously, a reaction temperature within the range of from about 180°–190° (preferably, 185°–188°) is employed.

In a preferred embodiment of the invention, the amount of HF source materials present in the reaction mixture is such as to provide less than 0.010 grams of HF per 100 grams of KF present therein. It is also preferred that the total amount of $K_2CO_3$ and $KHCO_3$ present in the reaction mixture be less than 0.2 grams per 100 grams of KF.

Preferred stirring rates are at least 50 rpm in baffled reaction vessels and at least 300 rpm in unbaffled vessels, using a blade or impeller type stirrer.

Preferred overall KF to chloro-pyridine ratios in the reaction mixture are such as to provide from about 110 to about 115% of the stoichiometric requirement of KF for complete conversion of the 2,6-dichloro- and/or 2-chloro-6-fluoropyridine to 2,6-difluoropyridine.

Preferred initial concentrations of the chloropyridine reactant(s) in the liquid phase of the reaction mixture are from about 2 to about 3 moles per liter.

DETAILED DESCRIPTION

It is critical to the attainment of practical reaction rates that the solvent employed as the reaction medium be DMSO. It is not known to what extent properties other than relative basicity and solvent ability are involved, but it has been found that the rate at which chlorine substituents in the 2 and 6 positions on pyridine rings are replaced by KF-derived fluorines is dependent on the solvent employed. In one instance, for example, the rate in DMSO was about 2.7 times the rate in sulfolane.

It is evident from the following tabulation that the solubility of KF in DMSO is quite low at ordinary ambient temperatures and is several fold lower at elevated temperatures. However, the rate at which the solubility decreases with increasing temperature drops off noticeably at about 125°. Also, the increase in reaction rate due to the higher proportion of molecules "activated" at 175°–190°, vis a vis 150°, of course is very substantial.

TABLE I

| Temperature | KF Solubility in DMSO Grams KF/100 Grams DMSO |
|---|---|
| 24° C. | 0.043 |
| 55 | 0.043 |
| 102 | 0.021 |
| 125 | 0.015 |
| 150 | 0.013 |

The reaction mixture does not have to be anhydrous and it is convenient to be able to use DMSO containing the amount of water (up to about 0.2%) commonly present in the reagent grade solvent. Water contents in the reaction mixture of up to about 0.5 weight percent of the amount of DMSO present can be tolerated, at least in short term operations where corrosion is less of a concern. However, it is generally advantageous that the reaction mixture contains substantially less than 0.3 grams of water per 100 grams of DMSO. Water contents in the solvent of less than about 0.2% are preferred and can be attained by drying over molecular sieves, by adding benzene and boiling off a water-benzene azeotrope or simply by distilling off a fore cut until the pot temperature is above the boiling point of water or of any known azeotrope of water with DMSO.

The amount of DMSO used should be sufficient to ensure facile stirring but is not otherwise critical. DMSO to dihalopyridine mole ratios of less than about 3–3.5 to 1 result in reaction mixtures (slurries) which are difficult to stir. A ratio within the range of about 4 to about 6 to 1 is preferred and corresponds to a concentration range of from about 3 to about 2 moles per liter of solution, respectively. Ratios up to 10 to 1, or even higher, may be employed but confer no advantage and are uneconomic.

The amount of KF introduced to the reaction mixture should be at least sufficient to provide the stoichiometric requirement of fluoride for the reaction, assuming complete conversion of the dichloro- or fluoro-chloro pyridine starting material to 2,6-difluoropyridine is desired. Although KF is not very soluble, the amount of KF in the reaction mixture is significant (together with average particle size) in determining the total KF surface area exposed to the DMSO/halopyridine solution. It is evident from the observed differences in reaction rates with and without intense stirring that the absolute rate of exchange of fluoride and chloride ions between the solid and liquid phases can be limiting upon the rate of exchange within the liquid phase. For this reason, it is beneficial to employ an excess of (finely comminuted) KF over the stoichiometric amount. On the other hand, as the amount of KF is increased, the amount of liquid phase required to avoid excessive stirring power requirements will also increase, so that the advantage of an excess of KF is, in effect, self-limiting. In general, an amount of KF equal to about 105–125 percent of the stoichiometric requirement will be satisfactory. Amounts equivalent to 250% or more of the stoichiometric amount may be used but little or no advantage is realized by going beyond an excess of about 25% over the stoichiometric quantity (100%).

It is critical to the practice of the invention that the amounts of HF-source materials, $KHCO_3$ and $K_2CO_3$ present in the reaction mixture be negligible. Preferably, no detectable amounts of these materials are present. It has been found that attainment of the requisite low level of HF-source materials cannot be assured simply by using reagent grade KF. It is apparent from the following tabulation that HF contents can vary substantially between different batches of the same grade of KF from the same supplier and that the use of technical grade KF is not necessarily ruled out.

tively will usually be quite satisfactory. In any case, the stirring or pumping rate must be such that the distribution of the solid phase in the reaction mixture is essentially uniform, as defined earlier herein.

Suitable reaction temperatures range from about 175° to about 192° C. At temperatures substantially below 175°, the reaction rate is so low as generally to be uneconomic and at temperatures substantially above 189° superatmospheric pressures are required and solvent oxidation and decomposition becomes a serious problem despite the absence of HF. In fact, at temperatures of about 175° or more, it is only because the evolved product vapors tend to displace atmospheric gases (oxygen), that it is not essential to pass a stream of a non-oxidizing or inert gas through the reaction vessel.

Pressure is not a critical parameter of the reaction and sub- or supra-atmospheric pressures may be employed. However, atmospheric or ambient pressures are most convenient and are accordingly preferred. If it is desired to operate at a temperature above the normal boiling point of the reaction mixture, it will of course be necessary to provide for operation under a pressure at least equal to the autogenous pressure of the reaction mixture.

In accordance with known principles, the contact

TABLE 2

Effect of KF Composition

| KF Used | Supplier | Grade | Batch or lot | Assay % KF | % HF[1] Supplier Specs. | % HF[1] By Analysis | Other Impurities % Cl[−] | Other Impurities % $CO_3^=$ | Results[3] in Reaction |
|---|---|---|---|---|---|---|---|---|---|
| A | MC&B | Reagent | 5F05 | 99.3 | 0.005 | 0.001 | 0.001 | 0.1 | Good |
| B | MC&B | Reagent | 18 | 100.5 | 0.02 | 0.052 | 0.005 | 0.001 | Bad |
| C | MC&B | Technical | 16 | 96.5 | — | 0.001 | — | — | Good |
| D | J. T. Baker | Reagent | 427766 | 99.3 | 0.005 | 0.009 | 0.001 | — | Good |
| E | Allied | Purified | N347 | 99.53 | nil | 0.001 | 0.02 | 0.006 | Good |
| F | Harshaw[4] | Drum | 20 | 97.36 | — | 0.016 | — | 0.19[2] | Good |

Notes:
[1]Includes HF as such or as bifluorides.
[2]Reported as KOH basicity.
[3]In terms of desired vs undesired product makes.
[4]Gray colored.

Potassium fluoride is made commercially by the reaction of potassium carbonate and aqueous HF and according to *Kirk-Othmer Encyclopedia of Chemical Technology*, 2d ed., Interscience, N.Y., 9, p. 649) may contain both $KHCO_3$ and KHF. However, the latter compound exerts an HF vapor pressure of less than 5 mm Hg at 190° C. and therefore does not act significantly as an HF- source material at the temperatures employed in the process of the present invention. On the other hand, it has been found that the inclusion of even a small amount of $NH_4HF_2$, which completely dissociates at less than 200°, has a pronounced negative effect on the reaction.

The required intensity of stirring can be attained by any of several expedients well known to those skilled in the art. Exemplary of such expedients are baffling of reactor walls, higher rates of rotation of flat blade or propeller type impellers and use of high capacity centrifugal pumps for rapid slurry recirculation. As a general guide, an impeller rate of at least 50 rpm in a baffled reactor and of at least 300 rpm in an unbaffled reactor should be used. Usually, however, rates of at least 60 and 450 rpm are respectively preferred for baffled and unbaffled reactors. The ultimate limits on stirring rates are those imposed by such considerations as power requirements, inherent equipment limitations and cavitation tendencies. However, rates of about 100–150 and 550–650 rpm in baffled and unbaffled reactors respectime required to attain any desired conversion of the dihalopyridine reactant to 2,6-difluoropyridine will depend on the temperature, the activities of the reactants in the liquid phase, and the relative amounts of 2,6-dichloro- and 2-chloro-6-fluoropyridine present in the starting material. Approximate rate constants, $k_1$ and $k_2$, for the successive reactions of 2,6-dichloro- and 2-chloro-6-fluoropyridine with fluoride in DMSO at several temperatures are given below:

TABLE 3

Kinetic Data

| Average Temperature ° C. | $k_1$ | $k_2$ | Stirring Speed (Unbaffled Reactor) |
|---|---|---|---|
| 150 | 0.136 hr$^{-1}$ | 0.036 hr$^{-1}$ | 488 |
| 180 | 1.00 | 0.295 | 455 |
| 186 | 1.33 | 0.40 | 455 |

In accordance with the known corrosiveness of KF solutions, it is advisable to use acid resistant materials of construction in any apparatus to be employed in the practice of the present invention. Such materials are familiar to practising chemical engineers.

The following examples are for purposes of illustration and are not to be construed as limiting the present invention to an extent not consistent with the claims appended with these specifications.

EXAMPLES

EXAMPLE 1

Into a 500 ml, 3-necked flask fitted with a paddle type stirrer, a thermometer and a 1 inch I.D., 10-tray Oldershaw column, was placed 73.93 g. (0.4995 moles) of 2,6-dichloropyridine, 200 ml of DMSO (dried over type 4A molecular sieves) and 66.04 g. (96.5% assay, 1.097 moles) of anhydrous, powdered KF (tech. grade; 0.001% HF; C, in Table 2; vacuum dried 8 hours at 100° C.). About 400 5 mm glass beads were added to improve stirring efficiency and the Oldershaw column was fitted with an overhead thermometer and take-off head leading to a receiver cooled in an ice-water bath. The mixture in the flask was stirred at 455 rpm while heating to reflux over a period of 40 minutes and then while refluxing for 9.4 hours at an average temperature of 186° C. The evolved difluoropyridine was distilled off as formed, the heat to the reaction being adjusted to maintain a moderate reflux return to the kettle at a head temperature of about 125° (except at the end of the reaction period, when the head temperature approached 140°C.).

There was obtained 56.16 grams of overhead which was found by vpc (vapor phase chromatography) to contain 55.08 g (95.9% of theory) of 2,6-difluoropyridine, plus a trace of 2-chloro-6-fluoropyridine and 1.03 g. of solvent decomposition products (primarily dimethyl sulfide and bis(methylthio)methane). Analysis of the material in the reaction flask showed that all of the 2,6-dichloropyridine had been converted and that 0.31 g. of 6-chloro- and 0.33 g. of 6-fluoro-2-(methylthio)-pyridines had been formed (0.38 and 0.46% yields, respectively).

EXAMPLE 2

In an essentially identical manner to the foregoing example, 0.4998 mole of 2,6-dichloropyridine was reacted with 1.06 moles of anhydrous, granulated KF (HF analysis 0.005%) for 8.6 hours in DMSO at 186° C. A 96.3% distilled yield of 2,6-difluoropyridine (based on the dichloropyridine charged) was obtained. Also formed were 0.44 g. of solvent degradation products and 0.19 g. of methylthio-substituted pyridine by-products.

EXAMPLE 3

In a similar manner, except that no glass beads were used, approximately 0.50 mole portions of 2,6-dichloropyridine were reacted with two different potassium fluorides (1.50 moles each) analyzing for 0.001 and 0.052% HF. These two reactions were run side-by-side, taking every precaution to make the conditions as identical as possible. After 10.25 hours at reflux, the 0.001% HF salt gave a 96.4% distilled yield of 2,6difluoropyridine along with 0.63 g. of solvent decomposition products and 0.40 g. of methylthio substituted pyridines. In contrast, the 0.052% acid salt gave only 64.1% product, plus 2.31 g. of solvent decomposition products and 2.11 g. of methylthio substituted pyridine by-products. The conversion of starting material was 99.8%, versus 100% with the 0.001% acid salt. This example shows that the presence of only 0.05% HF in the KF can lead to a greatly diminished yield of product and significantly higher amounts of undesirable side products.

EXAMPLE 4

In a manner similar to that of Example 1, 0.5001 mole of 2,6-dichloropyridine was reacted with 1.100 mole of anhydrous KF (0.052% HF, or 0.00166 moles HF) neutralized by the addition of 0.0125 mole of dry, powdered potassium hydroxide. After 10.0 hours at reflux there was obtained a 94.7% distilled yield of 2,6-difluoropyridine. The amounts of solvent decomposition products (1.68 g.) and of methylthio substituted pyridines (0.40 g.) produced are significantly lower than found in the absence of base (Example 3). This example illustrates that the adverse effects of HF can be effectively limited by the addition of a base to the reaction mixture. The amount of free base present after neutralization of the HF was equivalent to 0.276 grams of KOH per 100 grams of DMSO in the reaction mixture. Other bases, such as NaOH or Ca(OH)$_2$ may be used to neutralize HF present as such or generated from HF-source materials during the reaction.

EXAMPLE 5

In a manner identical to that of Example 1, 0.5005 mole of 2,6-dichloropyridine was reacted with 1.106 moles of dry potassium fluoride (analyzing at 0.001% HF). After 2.5 hours at reflux, approximately 36% of the theoretical amount of 2,6-difluoropyridine had distilled, indicating that the reaction was proceeding as expected for a low HF salt. The reaction mixture was then rapidly cooled to 40° C. and 2.00 g. of ammonium bifluoride added to the flask as a source of hydrogen fluoride. The mixture was again brought to reflux; after an additional 6.5 hours, VPC analysis indicated a distilled yield of 81.0% 2,6-difluoropyridine. In addition, 6.38 g. of solvent degradation products and 10.09 g. of methylthio substituted pyridine by-products were formed along with an estimated 5–6 g. of paraformaldehyde and an equal weight of water (the latter two materials also resulting from the decomposition of the DMSO solvent). This example clearly shows that the addition of hydrogen fluoride to a potassium fluoride salt normally giving good results will lead to a reduced product yield and large amounts of undesirable side products. (The thermal dissociation of ammonium fluoride to hydrogen fluoride and ammonium fluoride at temperatures of less than 200° C. is well known.)

EXAMPLE 6

In a similar manner, except that the reaction was carried out at 675 mm. of mercury pressure, 0.4994 mole of 2,6-dichloropyridine was reacted with 1.119 moles of anhydrous potassium fluoride (analyzing at 0.001% HF) for 13.5 hours at reflux. By analysis, 2,6-difluoropyridine and 2-chloro-6-fluoropyridine were produced in yields of 91.7% and 1.5%, respectively. The lower reaction temperature (averaging 180° C.) gave lower amounts of solvent degradation products (0.21 g.) and methylthio substituted pyridines (0.25 g.) than is normally encountered when the reaction is carried out at atmospheric pressure. This reduction in the amounts of by-products is, of course, accompanied by a corresponding decrease in the reaction rate.

EXAMPLE 7

In an effort to further supress solvent alteration, a run was made in which K$_2$CO$_3$ (0.5 mole percent, based on the KF) was added. It was evident, from the yields (19.3 and 65.3%, respectively) of difluoro- and chlorofluoropyridine products obtained after 5.4 hours at reflux, that the formation of the difluoropyridine is slowed down by the presence of this base (or of $KHCO_3$ formed therefrom — a thermally instable material). Thus, $K_2CO_3$ and $KHCO_3$ do not appear to be suitable bases for HF neutralization or solvent (DMSO) stabilization. The reaction mixture should not contain more than 0.5 grams of either or both of these bases per 100 grams of KF present therein.

What is claimed is:

1. In the process of preparing 2,6-difluoropyridine by reacting KF with an alpha-chloropyridine which is 2,6-dichloro- or 2-chloro-6-fluoropyridine, in dimethyl sulfoxide (DMSO) at an elevated temperature, essentially in the absence of initiators or catalysts, and distilling out the difluoropyridine as formed, the improvement whereby distilled difluoropyridine yields of at least 90% can be attained in reaction periods of 15 hours or less, without employing large excesses of KF or temperatures so elevated as to result in substantial DMSO alteration, said improvement comprising carrying out the reaction by:

a. providing a mixture of solid KF particles and a solution, in DMSO, of said alpha-chloropyridine, said mixture containing
   1. less than such amount of any HF source materials as to provide a total of 0.015 grams of HF per 100 grams of KF,
   2. a total of less than 0.5 grams of $K_2CO_3$ and $KHCO_3$ per 100 grams of KF,
   3. less than 0.5 grams of water per 100 grams of DMSO; and
b. intensely stirring said mixture and maintaining the temperature thereof within the range of from about 175° to about 192°.

2. The process of claim 1 in which the temperature of the reaction mixture is kept within the range of from about 180° to about 190°.

3. The process of claim 2 in which the said temperature is within the range of from about 185°–188°.

4. The process of claim 1 in which the amount of HF-source materials present in the reaction mixture is such as to provide less than 0.010 grams of HF per 100 grams of KF therein and the total amount of $K_2CO_3$ and $KHCO_3$ present is less than 0.2 grams per 100 grams of KF.

5. The process of claim 1 in which the amount of KF present in the reaction mixture is such as to provide from about 105 to about 125% of the stoichiometric KF requirement for complete conversion of said alpha chloropyridines present therein to 2,6-difluoropyridine.

6. The process of claim 5 in which the amount of KF is such as to provide from about 110 to about 115% of said stoichiometric KF requirement.

7. The process of claim 1 in which a baffled reactor is employed and the stirring rate is at least 60 rpm.

8. The process of claim 1 in which an unbaffled reactor is used and the stirring rate is at least 450 rpm.

9. The process of claim 1 in which the water content of the reaction mixture is less than 0.2 grams per 100 grams of DMSO present therein.

10. The process of claim 3 in which the reaction mixture contains
    1. less than 0.2 grams of water per 100 grams of DMSO,
    2. less than an amount of HF- source materials such as to provide 0.010 grams of HF per 100 grams of KF,
    3. a total of less than 0.2 grams of $K_2CO_3$ and $KHCO_3$ per 100 grams of KF, and
       a baffled reactor is used and the stirring rate is at least 60 rpm, or
       an unbaffled reactor is used and the stirring rate is at least 450 rpm.

* * * * *